Figure 1:
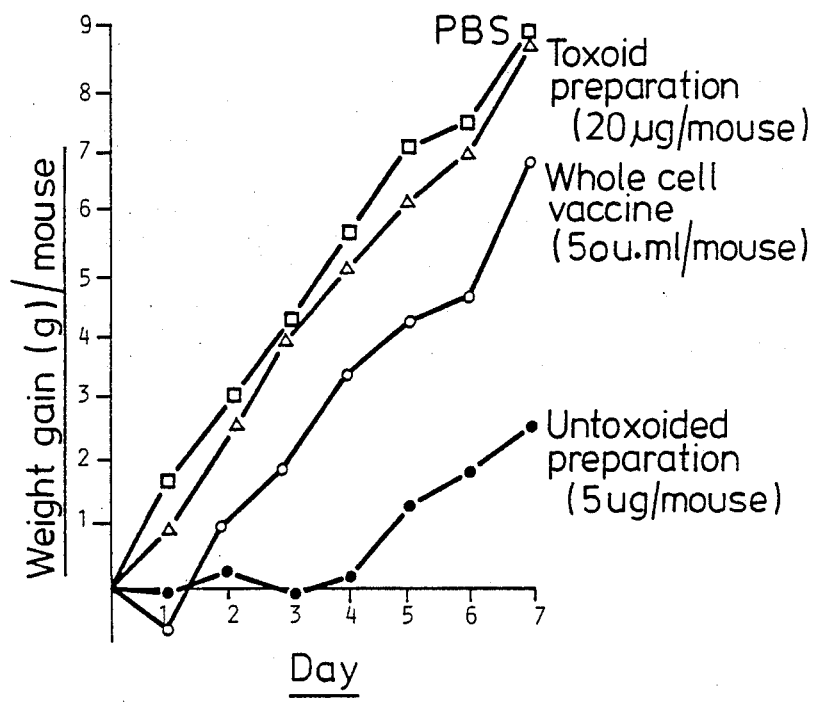

United States Patent [19]

Parton et al.

[11] Patent Number: 4,788,058

[45] Date of Patent: Nov. 29, 1988

[54] *B. PERTUSSIS* VACCINE PRODUCTION USING CARBODIIMIDES

[75] Inventors: Roger Parton, Jordanhill; Duncan E. S. Stewart-Tull, Uddingston, both of Scotland

[73] Assignee: The University Court of the University of Glasgow, Scotland

[21] Appl. No.: 866,157

[22] Filed: May 21, 1986

[30] Foreign Application Priority Data

May 22, 1985 [GB] United Kingdom ............... 8512972

[51] Int. Cl.$^4$ .............................................. A61K 39/10
[52] U.S. Cl. ........................................ 424/92; 424/88; 435/68; 435/822; 530/405; 530/409; 530/413
[58] Field of Search ................ 424/92, 88; 435/68, 435/822; 530/409, 405, 413

[56] References Cited

U.S. PATENT DOCUMENTS

| | | | |
|---|---|---|---|
| 3,098,693 | 7/1963 | Sheehan | 530/409 X |
| 3,619,371 | 11/1971 | Crook et al. | 424/88 X |
| 3,794,630 | 2/1974 | Mullan et al. | 530/405 X |
| 3,825,525 | 7/1974 | Mullan et al. | 530/405 X |
| 4,247,452 | 1/1981 | Irons et al. | 424/92 X |
| 4,314,993 | 2/1982 | Wijnendaele | 424/92 |
| 4,411,888 | 10/1983 | Klipstein et al. | 424/92 |
| 4,455,297 | 6/1984 | Syukuda et al. | 435/68 X |
| 4,546,161 | 10/1985 | Harvey et al. | 530/413 X |
| 4,687,738 | 8/1987 | Ginnaga et al. | 424/92 X |

OTHER PUBLICATIONS

Pharmacology & Therapeutics, 19, 1–53 (1983), Wardlaw et al.

*Primary Examiner*—Howard E. Schain
*Attorney, Agent, or Firm*—Stephen G. Rudisill

[57] ABSTRACT

The present invention provides a method of preparing a substantially non-toxic immunogenic preparation of pertussis toxic comprising treatment of pertussis toxin with a carbodiimide. The preparation may be used for vaccination against whooping cough as well as making vaccines for use in immunization against whooping cough. Desirably the pertussis toxin is treated in the form of an intimate admixture with filamentous.

14 Claims, 3 Drawing Sheets

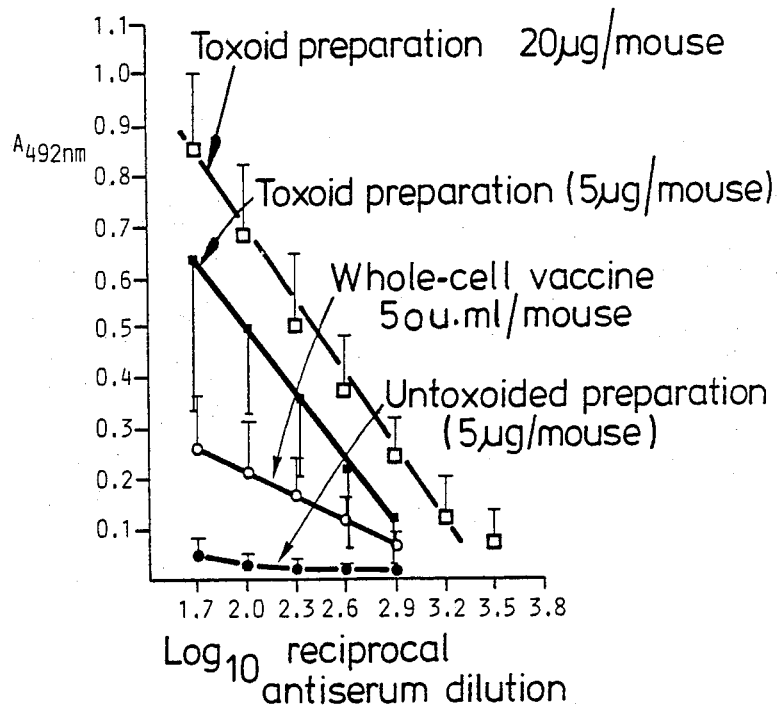

B. PERTUSSIS VACCINE PRODUCTION USING CARBODIIMIDES

BACKGROUND OF THE INVENTION

The present invention relates to the preparation of vaccines and in particular to the preparation of a vaccine against *Bordetella pertussis* (hereinafter *B. pertussis*) which causes whooping cough, as well as vaccines produced by the process of the invention.

In the past whooping cough vaccines have been based on the use of inactivated *Bordetella pertussis* (*B. pertussis*) cells. Since these contain active toxins and relatively large amounts of material which may not contribute to the stimulation of protective antibodies their potency is limited on the one hand whilst on the other hand the risk of undesirable side reactions is increased. More recently there has been proposed a method for the production of *B. pertussis* vaccine which involves the extraction of filamentous haemagglutinin (hereinafter FHA) and lymphocytosis-promoting factor (hereinafter LPF) antigens from *B. pertussis* cells followed by toxoiding treatment with formaldehyde or glutaraldehyde. It appears though that the detoxification or toxoiding of these antigens is either not complete or is not irreversible. Moreover the procedures used for extracting the antigens which include sucrose density gradient centrifugation are relatively cumbersome and expensive.

It is an object of the present invention to avoid or minimize one or more of the above disadvantages.

It has now been found that *B. pertussis* antigens can be successfully toxoided without significantly impairing immunogenicity, by treatment thereof with a carbodiimide. On the contrary it has now surprisingly been found that immunogenicity is substantially enhanced by the carbodiimide treatment.

Thus the present invention provides a method of preparing a substantially non-toxic immunogenic preparation of pertussis toxin comprising treatment of pertussis toxin with a carbodiimide.

Desirably the pertussis toxin is treated in the form of an intimate admixture of the pertussis toxin (PT) and filamentous haemagglutinin (FHA).

In further preferred aspects the present invention provides a method of preparing a *B. pertussis* vaccine comprising the steps of preparing an immunogenic toxoided pertussis toxin by a method of the invention, and formulating it in a physiologically acceptable carrier, as well as a vaccine prepared by said method.

In another preferred aspect the present invention provices a process for the production of a *B. pertussis* vaccine comprising the steps of:

culturing *B. pertussis* cells in a culture medium allowing said cells to release haemagglutinin (FHA) and pertussis toxin (PT) antigens into said culture medium;

recovering said FHA and PT antigens from said culture medium substantially free of cells and endotoxin;

treating said FHA and PT antigens with a water-soluble carbodiimide so as to detoxify them substantially; and formulating it is a physiologically acceptable carrier.

For the avoidance of doubt it is noted that pertussis toxin (PT) is also known in the art as lymphocytosis promoting factor (LPF) or lymphocytosis promoting factor-haemagglutinin (LPF-HA), as well as histamine sensitizing factor (HSF), pertussigen, pertussis ADP-ribosyl transferase, and islets activating protein. According references herein to PT correspond to references to LPF and any of the other names under which this antigen is known.

Also endotoxin is often referred to as lipopolysaccharide (LPS)—corresponding to the nature of this material.

The PT and FHA antigens may be obtained from cells of any suitable strain of *B. pertussis* that is available though desirably there is used a strain corresponding to that present in the environment in which the subjects to be vaccinated reside.

In connection with the above it should be noted that in accordance with the present invention there may be used either naturally occurring microorganism cells or genetically modified and/or synthetic genetically equivalent *B. pertussis* cells and references to microorganism cells herein are to be construed accordingly. Various procedures for producing such cells are well known in the art (see for example T. Mamatis et al (1982) "Molecular Cloning, a Laboratory Manual", Cold Spring Harbor, New York).

The cells may be cultured in any culture medium suitable for the culturing of *B. pertussis* cells under conditions conducive to growth and division of the cells, and production of PT and FHA, such media and conditions being well known in the art. In general there is used an aqueous medium at a temperature of from 30° C. up to 40° C. at a pH of from 7.0 to 8.0.

Once a sufficient amount of PT and FHA antigens has been released into the culture medium from the growing *B. pertussis* cells, generally after from 2 to 5 days, the culture medium is separated from the cells by centrifugation at a rate sufficient to sediment the cells within a reasonable period of time, e.g., 10,000 g for 30 minutes.

The P.T. and F.H.A. antigens may be recovered from the culture medium by any suitable method which does not significantly impair their immunogenicity. In accordance with the present invention it has been found that both P.T. and F.H.A. can be recovered generally free of other cell products and toxic components (such as LPS) in a single unitary extraction procedure based on selective affinity chromatography or dye-ligand chromatography using an immobilized triazine as the ligand. In this connection it is to be understood that freedom from toxic components means removal of such components either more or less completely or merely to the extent that any residual such components are substantially detoxifiable by the carbodiimide treatment.

Any suitable carrier may be used for the triazine in the above extraction procedure though conveniently there is employed a polysaccharide. A suitable commercially available product comprises Blue Sepharose (e.g. Type CL-6B available from Pharmacia Ltd., Sweden) which contains a blue triazine dye-ligand.

The dye-ligand chromatography may be carried out under an conditions conducive to retention of the P.T. and F.H.A. antigens which do not significantly impair their immunogenicity. In the case of Blue Sepharose selective affinity material the substantially cell-free culture medium is generally brought into intimate admixture with said selective affinity material at a pH in the range from 5.5 to 8.5, e.g. about pH 6.0.

The culture medium supernatant fluid containing unbound cell products and components is then discarded following which the bound P.T. and F.H.A is eluted using eluant of sufficiently great ionic strength to release these antigens from the dye-ligand material. In the case of Blue Sepharose there is conveniently used an 1M aqueous sodium chloride or similar eluant. Conveniently, column fractions containing the desired P.T. and F.H.A. antigens may be identified by means of positive haemagglutination of horse erythrocytes.

In accordance with the present invention the P.T. containing material is treated with a carbodiimide. Suitable carbodiimides comprise compounds of the general formula R—N=C=N—R' wherein R and R' are the same or different and each can be optionally substituted alkyl or aryl. Preferably R and R' are selected from lower alkyl (e.g. akyl having 1 to 4 carbon atoms) and optionally substituted phenyl. A particularly suitable diimide that may be mentioned is 1-ethyl-3-(3-dimethylaminopropyl)-carbodiimide (hereinafter EDAC). In general the carbodiimide is used in the form of an acid addition salt, e.g., hydrochloride, thereof. The carbodiimide treatment is continued until the toxicity of the toxin has been substantially eliminated. The toxicity of the treated material can be readily monitored by various tests known in the art including for example histamine sensitizing activity and leucocytosis promoting ability in the mouse which methods are further described in the accompanying example and in the literature. The required duration of the toxoiding treatment can be varied in accordance with the pH which is generally in the range from 4.0 to 8.0 and the temperature which is generally in the range from 4° to 30° C. and the nature and concentration of the carbodiimide used. In the case of EDAC treatment is generally carried out at weakly acid pH in the region from pH 4.0 to pH 6.0 at a temperature of from 15° to 25° C. Using an EDAC concentration of from 5.0 to 30.0 mM, treatment is generally carried out for from 6 to 25 hours.

When the toxicity has been sufficiently reduced, any remaining carbodiimide may be conveniently removed by dialysis or any other suitable method known in the art.

The vaccines of the invention are generally administered parenterally, especially via the intramuscular or subcutaneous routes of injection, or orally. For parenteral administration the vaccine may be presented in sterile solution or suspension in aqueous or oleaginous vehicles, which may also contain preservatives and material for rendering the solution or suspension isotonic with the blood of the intended recipient e.g. 0.15 aqueous sodium chloride. Such formulations may conveniently be presented in unit-dose or multi-dose sealed containers.

For oral administration the vaccine may be presented as a draught in water or in a syrup, in capsules, cachets, boluses or tablets, as an aqueous or oleaginous solution or suspension or in suspension in a syrup, such suspensions optionally including suspending agents or as an oil-in-water or water-in-oil emulsion. Where desirable or necessary flavouring, sweetening, preserving, thickening or emulsifying agents may be included in the formulation.

Tablets may contain the antigen preparation as a powder or granules for example a freeze-dried powder or granules optionally mixed with binders, lubricants, inert diluents or surface-active or dispersing agents and may be formed by compression or by mouling in inert liquid diluent. Such tablets may be optionally scored and/or coated. Capsules and cachets may contain the active compound alone or in admixture with one or more accessary ingredients. Capsules may also contain the active compound in aqueous or oleaginous solution suspension or emulsion optionally in association with accessor ingredients.

In general the vaccines of the invention are formulated so that the antigens are presented in the solution or suspension at a concentration of from 10 to 100 ug protein/ml. When presented in unit dosage form, each dose conveniently containing from 0.1 to 1.0 mls, it is generally preferred that each dose contains from 10 to 20 ug of the antigens. It will be appreciated that the relative proportions of the PT and FHA antigens may be varied in the vaccine. In general though it is desired that the relative proportions of PT and FHA, respectively are in the range from 10:1 to 1:10.

If desired the vaccine of the invention may conveniently also be formulated as a combined or conjugate vaccine containing antigens for stimulating protection against one or more other diseases such as for example diphtheria and/or tetanus toxoids. Desirably the vaccine of the invention is also formulated with an effective dosage of one or more adjuvants or immunopotentiating agents such as for example Alhydrogel, muramyl dipeptide (MDP) or one of its derivatives, or purified Saponin (Quil-A).

The present invention also provides a process for producing a pharmaceutical formulation of a vaccine of the invention comprising bringing into association the vaccine and a pharmaceutically acceptable carrier therefore.

The vaccines of the invention may be administered to human beings to prevent whooping cough in accordance with any vaccination schedule suitable for vaccination against whooping cough. The dosage administered and schedule followed depends on the antigenicity and immunogenicity of the antigens therein and on other well-known pharmaceutical considerations such as the age and bodyweight of the subject. It is recommended that the vaccine is given at 2–6 months of age in at least 2 doses separated by an interval of from 4 to 6 weeks, preferably followed by a booster dose at 18 months and at 5 years, though the number of doses may be reduced by at least some extent depending on the degree of immunopotentiation resulting from the toxoiding process of the invention and the inclusion of adjuvants and/or other immunopotentiating agents.

In a further aspect of the present invention there is therefore provided a method of preventing whooping cough comprising the administration of an effective immunogenic dose of a vaccine of the invention or a pharmaceutical formulation thereof to a human being.

Further preferred features and advantages of the invention will appear from the following examples given by way of illustration only.

Example I—Preparation of *B. pertussis* Vaccine

A. Preparation of Toxins

*Bordetella pertussis* isolated from childhood hooping cough in Glasgow designated *B. pertussis* ASB1 was cultured using a modified Stainer and Scholte medium containing:

|  | grammes/liter |
|---|---|
| L-glutamate (monodosium salt) | 10.72 |
| L-proline | 0.24 |
| NaCl | 2.50 |
| $KH_2PO_4$ | 0.50 |

| | grammes/liter |
|---|---|
| KCl | 0.20 |
| $MgCl_2 \cdot GH_2O$ | 0.10 |
| $CaCl_2$ | 0.02 |
| Tris | 1.52 |
| L-crysteine HCl | 0.04 |
| $FeSO_4 \cdot 7H_2O$ | 0.01 |
| Ascorbic acid | 0.02 |
| Nicotonic acid | 0.004 |
| Glutathione | 0.10 |

The medium (500 ml) in 1 liter Fernbach flasks) was inoculated from growth on Bordet-Gengou agar plates and incubated at 37? C. for 5 days.

Organisms were removed by centrifugation twice at 10,000 rpm ($\times 14,300$ g) for 30 min at 4° C. The pH of the remaining, cell-free culture fluid, was adjusted to 6.0 with 2.5N HCl and thimerosal 0.01% (W/V final concentration) (Sigma Products, U.S.A.) was added as preservative.

Blue Sepharose CL-6B (Pharmacia Ltd., Sweden) was added (10 ml of packed gel per liter of culture fluid) and stirred slowly at 4° C. for 18 hr. The culture fluid was then separated off from the gel and discarded and the gel was poured into a glass column and washed with several column volumes of 0.05M Tris-HCl buffer at pH 8.0 at room temperature.

The B. pertussis antigens were eluted from the column with 0.05M Tris HCl buffer at pH 8.0 made up to 1M NaCl ionic strength, 5 ml fractions of column eluate were collected and those which caused positive haemagglutination with horse erythrocytes were pooled, concentrated and stored at $-20°$ C.

The B. pertussis antigen preparation thus obtained was dialyzed overnight against 2 liters of 20.0 mM sodium phosphate buffer made to 0.5M NaCl at pH 5.0 to lower the pH in order to facilitate the toxoiding treatment.

B. Toxoiding Procedure

To each 50 ug of total protein present in the final volume of toxoiding mixture, 4.0 mg of 1 ethyl-3-(3-dimethylaminopropyl)-carbodiimide HCl (EDAC) was added. The carbodiimide was dissolved in 20.0 mM sodium phosphate buffer made to 0.5M NaCl at pH 5.0. The final volume of toxoiding mixture was adjusted such that it contained 50 ug *B. pertussis* antigen protein and 4.0 mg EDAC $ml^{-1}$ of mixture. The treatment mixture was allowed to stand for 24 hours at 37° C.

C. Preparation of Vaccine for Injection

The toxoided antigens were dialyzed exhaustively against 20.0 mM sodium phosphate buffer made to 0.5M NaCl in the presence of 0.01% (W/V) thimerosal to remove the carbodiimide. The resulting suspension was then made up in sterile phosphate buffered saline (NaCl $8gl^{-1}$, KCl 0.2 $gl^{-1}$, $KH_2PO_4$ 0.2 $gl^{-1}$ and $Na_2HPO_4$ 1.15 $gl^{-1}$).

Example II—Properties of Vaccine

The vaccine preparation comprised predominantly a mixture of filamentous haemagglutinin (FHA) and pertussis toxin (LPF-HA or PT) with some other minor antigens also present.

Toxicity

The leucocytosis promoting ability was tested by injection into mice. No increase in the white blood cell count was found with a dose of 4.0 ug toxoided antigen protein/mouse. Histamine sensitizing activity was tested by challenging mice 5 days after injection of the vaccine with 3.0 mg/mouse of histamine dihydrochloride. No detectable activity was found with 12.0 ug toxoided protein/mouse. No significant reduction in the rate of weight gain was found after administration of 4.0 ug toxoided antigen protein/mouse over 7 days.

In Vitro Activity

The toxoided *B. pertussis* antigens were found to be more active in the stimulation of anti-PT antibodies of the IgG class than the native, non-toxoided antigens upon analysis of the serum from mice by experimental serology.

The toxicity and activity determinations referred to above and in the following examples are further described in the review "*Bordetella pertussis* Toxins" by A. C. Wardlaw & R. Parton in Pharmacology & Therapeutics (1983) 19 pp. 1–53.

Example III—Preparation of *B. pertussis* vaccine

6 PT/FHA preparations were obtained using the procedure of Example I (2 batches), using a modified culture procedure in which methyl β-cyclodextrin (lg/l.) was added to a Stainer & Scholte medium as used in Example I and the medium shaken for 36 hours (2 batches), and a further modified culture procedure (Ionaizumi et al (1983) Infection & Immunity Vol. 41 pp. 1138–1143) in which a cyclodextrin liquid (CL) culture medium containing methyl β-cyclodextrin (1lg/l) was used in place of the Stainer Scholte medium of Example I and the medium again was shaken for 36 hours (2 batches).

The PT and FHA yields were determined using an ELISA system (Ref. 2) and as may be seen from Table I different proportions of PT and FHA were obtained by the various procedures.

All the batches were then pooled prior to toxoiding and vaccine formulation by the procedures described in Example I above.

Ref. I

Example IV—Properties of Vaccine

The toxicity and activity of the (pooled) PT/FHA vaccine obtained by the procedure of Example III were then compared with those of a standard whole cell whooping cough vaccine prepared by heating whole cells at 56° C. for 30 mins, and an untreated *B. pertussis* toxin preparation obtained by the first part of the procedure described in Example III i.e. omitting the carbodiimide treatment.

Table II details the results of the histamine-sensitizing activity test used to monitor the storage properties of the preparations of the invention and shows that under normal vaccine storage conditions (+4° C.) there was no reversion and loss of non-toxicity at immunogenic dose levels. It may on the other hand be noted that the toxin exhibited high toxicity even at very low, non-immunogenic, dose levels.

FIG. 1 of the accompanying drawings shows comparative data obtained using the mouse weight gain test. As may be seen the preparations of the present invention had little or no adverse effect as compared with phosphate buffered saline (PBS) controls, whereas even the standard whole cell vaccine substantially decreased the rate of weight gain.

Figure 2:
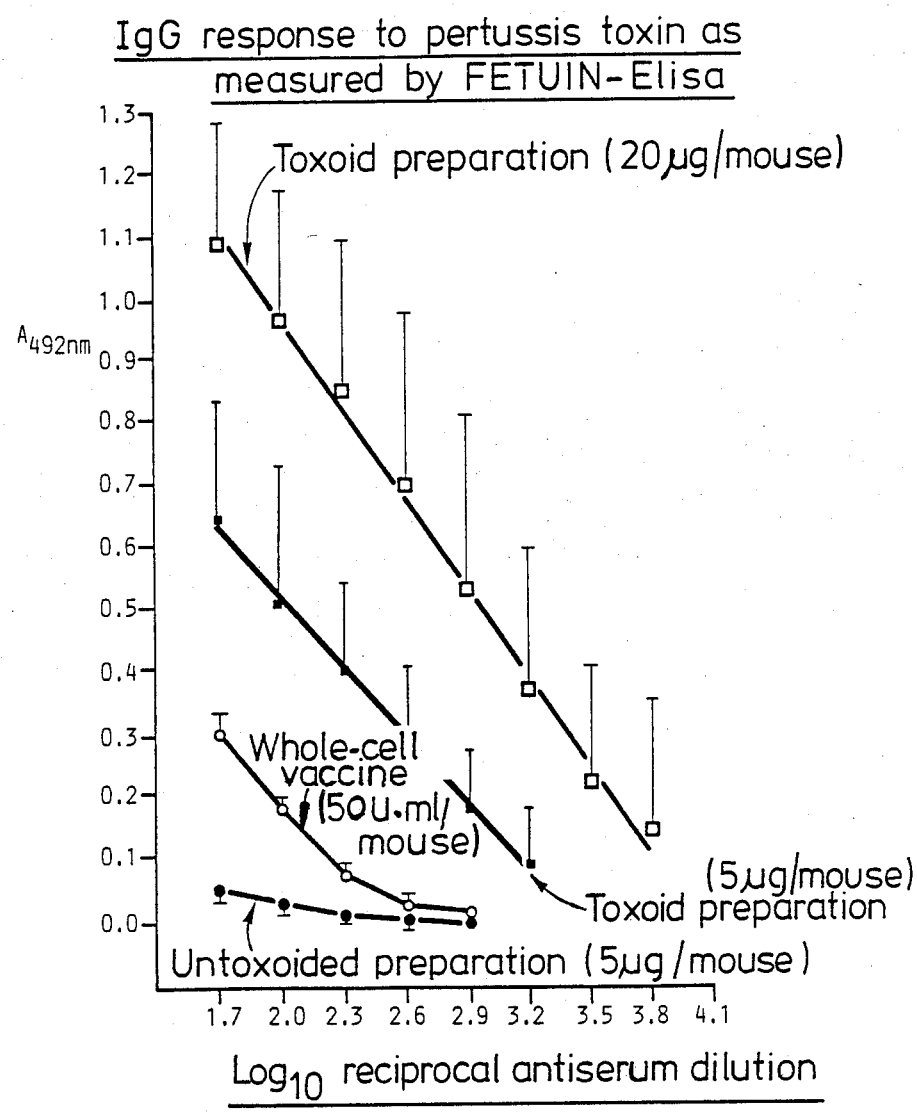

FIGS. 2 and 3 show the results of tests for the antigenicity of the preparation of the invention administered to mice at two different dose levels, in an ELISA assay (see for example E. Engvall et al (1980) in "Methods In Enzymology Vol. 70 pp. 419-439). In the case of FIG. 3 a modified system using Fetuin coated (400 nanograms per well) microtitre plates was employed. Substantially higher antigenicity was obtained than with standard whole cell vaccine (at 5 opacity units (ou) ml/mouse) or with the untreated preparation (at 5 ug/mouse).

Table III details the results of the in vivo mouse protection test. As shown in the Table three separate batches of the treated preparation were tested corresponding to three individually treated batches of the pooled antigen material obtained in the first part of Example III. The effective Protective Dose (PD 50) quoted for the untreated toxim preparation is of course extrapolated since this dose is well above the normal lethal dose for the untreated material.

TABLE I

| SAMPLE PT/FHA PREPARATIONS (BLUE SEPHAROSE ELUATES) | | | | |
|---|---|---|---|---|
| Expt. No. | Culture Conditions | PT ($\mu$g/ml by ELISA) | FHA ($\mu$g/ml by ELISA) | PT/FHA ratio |
| 1 | Stainer and Scholte medium, 5 days, static | 44 | 67 | 0.65 |
| 2 | | 64 | 70 | 0.91 |
| 3 | Strainer and Scholte medium + methyl $\beta$-cyclodextrin 36 h, shaken | 1126 | 114 | 9.9 |
| 4 | | 940 | 111 | 8.5 |
| 5 | Cl medium + methyl $\beta$-cyclodextrin 36 h, shaken | 238 | 380 | 0.63 |
| 6 | | 197 | 488 | 0.43 |

N.B. The PT/FHA preparation used for toxoiding was pooled material with a PT:FHA ratio of 1:1.

TABLE II

Stability of toxoided and non-toxoided preparation (Batch I) at $-20°$ C., $+4°$ C. and $+37°$ C. - Histamine-sensitizing activity

| Preparation | Dose per mouse | No. of survivors/No. challenged after storage for:- | | |
|---|---|---|---|---|
| | | 2 weeks | 4 weeks | 8 weeks |
| Standard whole-cell vaccine (4° C.) | 0.75 ou.ml | 0/5 | 0/5 | 0/5 |
| | 0.37 | 1/5 | 2/5 | 3/5 |
| | 0.18 | 3/5 | 4/5 | 4/5 |
| | 0.09 | 5/5 | 4/5 | 5/5 |
| Toxin ($-20°$ C.) | 0.16 $\mu$g | 1/5 | 0/5 | 0/5 |
| | 0.08 | 2/5 | 2/5 | 2/5 |
| | 0.04 | 3/5 | 4/5 | 3/5 |
| | 0.02 | 5/5 | 5/5 | 5/5 |
| Toxin ($+4°$ C.) | 0.16 $\mu$g | 2/5 | N.T. | 1/5 |
| | 0.08 | 3/5 | | 3/5 |
| | 0.04 | 5/5 | | 5/5 |
| | 0.02 | 5/5 | | 5/5 |
| Toxin ($+37°$ C.) | 0.64 $\mu$g | 0/4 | N.T. | 0/5 |
| | 0.32 | 1/5 | | 0/5 |
| | 0.16 | 2/5 | | 1/5 |
| | 0.08 | 3/5 | | 2/5 |
| Toxoid ($-20°$ C.) | 20 $\mu$g | 5/5 | N.T. | N.T. |
| | 10 | 5/5 | | |
| | 5 | 5/5 | | |
| | 2.5 | 5/5 | | |
| Toxoid ($+4°$ C.) | 20 $\mu$g | 5/5 | N.T. | 5/5 |
| | 10 | 5/5 | | 5/5 |
| | 5 | 5/5 | | 5/5 |
| | 2.5 | 5/5 | | 5/5 |
| Toxoid ($+37°$ C.) | 10 $\mu$g | 4/5 | 0/5 | 0/5 |
| | 5 | 5/5 | 3/5 | 3/5 |
| | 2.5 | 5/5 | 4/5 | 4/5 |
| | 1.2 | 5/5 | 5/5 | 5/5 |

N.B. The toxoid showed no sign of reversion when stored at 4° C. Some histamine-sensitizing activity was regained after 4 weeks at 37° C. but this was <1% of the original activity.

TABLE III

| Preparation | PD$_{50}$ (and 95% confidence limits) |
|---|---|
| Standard whole-cell vaccine | 0.31 ou.ml/mouse (0.702, 0.48) |
| Toxoid Batch I | 1.11 $\mu$g/mouse (0.8, 1.55) |
| Toxoid Batch II | 0.8 $\mu$g/mouse (0.56, 1.13) |
| Toxoid Batch III | 1.11 $\mu$g/mouse (0.75, 1.64) |
| Toxin | 1.32 $\mu$g/mouse (by extrapolation) |

Challenge Dose = 150 × LD$_{50}$

What is claimed is:

1. A method of preparing a substantially non-toxic immunogenic preparation of pertussis toxin comprising treatment of pertussis toxin with a carbodiimide, said pertussis toxin being in the form of an intimate admixture with filamentous haemagglutinin.

2. A method of preparing a substantiallly non-toxic immunogenic preparation suitable for use in vaccination against *B.pertussis* which method comprises treatment of pertussis toxin in intimate admixture with filamentous haemagglutinin, with an effective toxoiding amount of a carbodiimide.

3. The method of claim 2 which method includes the preliminary steps of providing B. pertussis cells and then isolating the pertussis toxin and filamentous haemagglutinin together from said cells.

4. The method of claim 3 wherein said isolation step is carried out so that said pertussis toxin and filamentous haemagglutinin are isolated substantially free of other cellular material and with substantially unimpaired antigenicity and immunogenicity.

5. A method of preparing a pertussis vaccine comprising the steps of preparing a preparation as claimed in claim 2 and formulating it in a physiologically acceptable carrier.

6. A process for the production of *B. pertussis* vaccine comprising the steps of:
   culturing *B. pertussis* cells in a culture medium;
   allowing said cells to release haemagglutinin (FHA) and pertussis toxin (PT) antigens into said culture medium;
   recovering said FHA and PT antigens together from said culture medium substantially free of cells and endotoxin;
   treating said FHA and PT antigens together, with a water-soluble carbodiimide so as to detoxify them substantially; and
   formulating the detoxified PT and FHA in a physiologically acceptable carrier.

7. A method as claimed in claim 6 wherein the PT and FHA antigens are recovered together from the culture medium by means of selective affinity chromatography or dye-ligand chromatography, using an immobilized triazine as the ligand.

8. A method as claimed in claim 7 wherein the triazine is immobilized on a polysaccharide carrier.

9. A method as claimed in claim 6 wherein the carbodiimide treatment is carried out at a pH of from 4.0 to 8.0 at a temperature of from 4° to 30° C.

10. A method as claimed in claim 9 wherein is used a carbodiimide concentration of from 5.0 to 30.0 mM.

11. A method a claimed in claim 10 wherein the carbodiimide treatment is carried out for from 6 to 24 hours.

12. A whooping cough. vaccine when prepared using a method according to claim 5.

13. A vaccine according to claim 12 which includes at least one of an adjuvant and an immunopotentiating agent.

14. A method of immunization against whooping cough or pertussis comprising the administration of an munogenically effective dosage of a vaccine according to claim 12.

* * * * *